United States Patent [19]

Norton et al.

[11] 4,059,694

[45] Nov. 22, 1977

[54] CARDIOTONIC AGENT

[75] Inventors: Ted R. Norton; Shoji Shibata; Midori Kashiwagi, all of Honolulu, Hawaii

[73] Assignee: The University of Hawaii, Honolulu, Hawaii

[21] Appl. No.: 710,534

[22] Filed: Aug. 2, 1976

Related U.S. Application Data

[63] Continuation-in-part of Ser. No. 683,446, May 5, 1976, abandoned.

[51] Int. Cl.$^2$ .................... A61K 37/00; C07C 103/52
[52] U.S. Cl. .................... 424/177; 260/112.5 R
[58] Field of Search .................. 424/177; 260/112.5 R

[56] References Cited

U.S. PATENT DOCUMENTS 3,951,939  4/1976  Fritz et al. .................... 424/177

FOREIGN PATENT DOCUMENTS 1,411,184  1/1973  United Kingdom ................ 424/177

OTHER PUBLICATIONS

Wunderer, et al., Eur. J. Biochem. 68, 193–198, 1976.
Beress, et al., Hoppe-Seyler's Z. Physiol. Chem. 357, 409–414, 1976.
L. Beress, et al., Toxicon, 1975, 13, pp. 359–367.
L. Beress, et al., Febs. Lit. 50, 1975, pp. 311–314.
G. Wunderer, et al., Hoppe-Seyler's Z. Physiol. Chem. 357, pp. 239–240, 1976.

*Primary Examiner*—Delbert R. Phillips
*Attorney, Agent, or Firm*—Walter Patton

[57] ABSTRACT

A peptide designated anthopleurin-A, hereinafter also referred to as AP-A, obtained from the sea anemone *Anthopleura xanthogrammica* is found to possess cardiotonic activity.

8 Claims, No Drawings

CARDIOTONIC AGENT

The invention described herein was made in the course of work under a grant from the Department of Health, Education and Welfare.

This application is a continuation-in-part of copending application Serial No. 683,446, filed May 5, 1976, now abandoned.

BACKGROUND OF THE INVENTION

Agents, currently used to stimulate the failing heart are limited by their toxic effects on the heart or by deleterious side effects on the peripheral circulation. For example, although the cardiac glycosides are myocardial stimulants and can restore the failing heart, they do so at doses very close to those which produce toxic symptoms of cardiac arrhythmia, nausea and vomiting. The use of sympathomimetic agents are limited by associated arrhythmia, tachycardia, tachyphylaxis or altered peripheral resistance.

The compound of this invention exhibits valuable pharmacological properties. It primarily affects the contractile force of the heart muscle. In particular, it has a potent cardiotonic action on the cardiac muscle of different animals in vivo and in vitro but does not have any demonstrable effect on the blood pressure, heart rate and vascular smooth muscle. The compound also causes a positive inotropic effect on atria under severe temperature stress, anoxia and in the presence of low $Ca^{++}$ concentrations. The cardiac glycosides are ineffective under these stressful conditions. These specifics positive inotropic properties of AP-A make it useful in the treatment of congestive cardiac failure.

Congestive heart failure results when the heart pumps less blood than is required by the metabolic demands of the body. The objectives of therapy are to restore the balance of supply and demand for blood. This can be achieved through the use of the instant cardiotonic agent which improves myocardial contractility and influences cardiac output to meet the demands of the body.

SUMMARY OF THE INVENTION

A novel peptide extracted from the sea anemone *Anthopleura xanthogrammica* has been discovered to have marked cardiac stimulant effects. Thus, it is the object of this invention to describe this novel peptide. It is a further object of this invention to describe the method of obtaining said novel peptide from sea anemone. A still further object is to describe compositions and the methods of treatment of heart failure utilizing said peptide. Further objects will become apparent upon reading the following description and claims.

DESCRIPTION OF THE INVENTION

The novel peptide of the present invention, anthopleurin-A (AP-A), is obtained from the sea anemone *Anthopleura xanthogrammica* collected from Bodega Bay, California.

The sea anemones are homogenized and extracted with water or with a solution of water and a water miscible organic solvent. The crude extract, containing anthopleurin-A, is subjected to gel filtration to give a forty-fold increase in purity of anthopleurin-A. Alternatively, semipermeable membranes may be used to accomplish the results obtained by gel filtration. Cation exchange chromatography provides an excellent separation of anthopleurin-A in a purity of about 30–80% depending on the particular collection of anemones. The balance is biologically inactive peptides and the buffer salts. To obtain analytically pure salt-free material the above material is further purified by gel filtration, cation-exchange chromatography and desalted. All the separation procedures in the present invention are monitored by bioassay using the isolated rat atria for determination of positive inotropic effort using the procedure described in the section headed Bioassay.

A preferred process for obtaining anthopleurin-A is by extracting the collected wet sea anemone *Anthopleura xanthogrammica* with water, alcohol or an aqueous-alcoholic mixture and subjecting the crude extract to gel filtration chromatography on a column packed with cross-linked dextran eluted with aqueous $NH_4HCO_3$ solution or other volatile salt solution. The active fraction is lyophilized and chromatographed on a column packed with a cation-exchange resin and eluted with a buffer or with a buffer and a gradient of an ionizable salt solution. A suitable solution for eluting the cation-exchange resin is phosphate buffer or phosphate buffer with a gradient of NaCl solution. The active fraction is lyophilized to obtain the purified anthopleurin-A. The lyophilized material is 1.0 to 1.4% anthopleurin-A, the balance being 0.2–2.0% inactive polypeptides, buffer salts and the ionizable salts. To obtain salt-free material, the dried material is chromatographed on a column packed with cross-linked dextran eluted with a salt solution to remove phosphate. The active fraction is collected and desalted by chromatographed on a column packed with cross-linked dextran resin eluted with a dilute solution of a lower organic acid, such as acetic acid.

To obtain analytically pure AP-A, the desalted material is subjected to gel filtration chromatography on a column packed with cross-linked dextran eluted with water and ion exchange chromatography on a column packed with sulfoethyl cellulose eluted with pyridine acetate buffers.

In a further preferred process for obtaining anthopleurin-A from *Anthopleura xanthogrammica*, the wet anemones are cut into pieces about 2 cm. in size, homogenized and extracted with 30% aqueous ethanol. The crude extract is concentrated to an aqueous solution, which is centrifuged to remove solids and partitioned with chloroform. The chloroform extracted aqueous solution is lyophilized and the residue subjected to gel filtration chromatography on a column packed with cross-linked dextran such as Sephadex G-50, having an exclusion limit of 30,000 for globular proteins (manufactured by Pharmacia Fine Chemicals, Box 175, S-751 04, Uppsala 1, Sweden), and eluted with 0.1M $NH_4HCO_3$. The fraction having Ve/Vo 1.84 to 2.57 contains anthopleurin-A purified forty-fold. The fraction Ve/Vo 1.84 to 2.57 is lyophilized and further purified by chromatography on a column packed with a weakly acidic cation exchange resin, such as CM-Sephadex C-25, eluted with a 0.03M, pH 7.5 phosphate buffer with gradient elution up to 0.5N NaCl. Anthopleurin-A elutes at Ve/Vo 2.99 to 3.39 and is lyophilized. The Ve/Vo 2.99 to 3.39 fraction is rechromatographed on a column packed with Sephadex G-50, having an exclusion limit of 30,000, and eluted with 0.017M acetic acid which is 0.03M in NaCl. The fraction eluted at Ve/Vo 1.66 to 2.16 is lyophilized to obtain anthopleurin-A substantially phosphate-free. The sodium chloride is removed by placing a sample on a column packed with a cross-linked dextran resin such as Sephadex G-10 having an exclusion limit of 700 followed by approximately three times sample volume of 20% sodium chloride solution, eluted with 0.017M acetic acid. Pure (30–80% AP-A), salt-free anthopleurin-A elutes at Ve/Vo 0.93 to 1.12. Since associated polypeptides were found to be inactive, this material is adequate for pharmacological studies.

To obtain AP-A free of associated inactive peptides, the Ve/Vo 0.93 to 1.12 fraction is dissolved in distilled water and chromatographed on Sephadex G-25, fine, in distilled water. Elution with distilled water produces the bulk of the active peptide (90%) 75% pure at Ve/Vo between 1.3 and 1.7, while the remainder of the active peptide is eluted pure with 0.2M NH₄OAc. The Ve/Vo 1.3 to 1.7 fraction is lyophilized, redissolved in distilled water and chromatographed on Cellex-SE cellulose (Bio.Rad Laboratories, Richmond, California), equilibrated with 0.05M pyridine adjusted to pH 2.7 with acetic acid. AP-A is eluted pure by a linear gradient of equal volumes each of 0.05M pyridine acetate pH 2.7 and 0.2M pyridine acetate pH 3.1 in an area corresponding to 0.1M pyridine acetate. This material now is analytically pure as judged by amino acid analysis and sequencing.

The preferred process for obtaining pure anthopleurin-A is illustrated by the following Scheme 1.

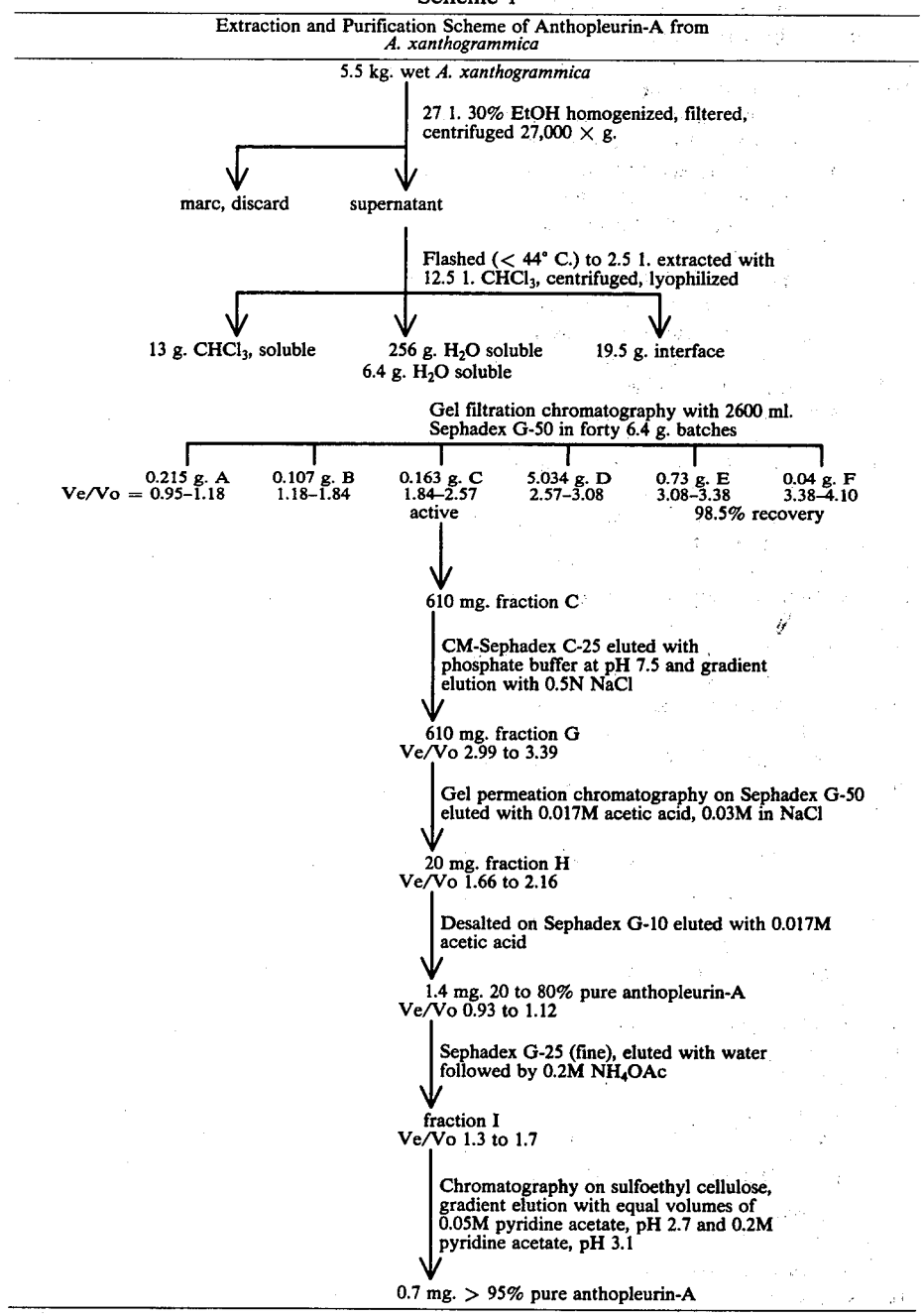

The novel peptide, AP-A, of this invention exhibits valuable pharmacological properties. It primarily effects the contractile force of the heart muscle. By increasing the contractile force of the heart muscle with the resultant increase in cardiac output, this compound affords a valuable means of treating heart failure.

The present novel peptide, AP-A, of this invention has been found to be a signficant myocardial stimulant which substantially avoids the toxic manifestations of prior art cardiac stimulants. This cardiac stimulation is observed in animals by measuring the in vitro contractile effect on isolated heart muscle and in vivo in anesthetized dogs fitted with a cardiac strain gauge.

The novel peptide, AP-A of the present invention is administered to the patient with heart failure at a rate of from about 0.01 to about 5 µg/kg. of body weight per hour.

For such usage the compound of this invention may be administered orally or parenterally as such or admixed with conventional pharmaceutical carriers. The parenteral route is preferred. It may be administered orally in such forms as tablets, dispersible powders, granules, capsules, syrups and elixirs, and parenterially as solutions, suspensions, dispersions, emulsions, and the like, e.g., a sterile injectable aqueous solution. The compound may also be altered chemically such as by acylation and esterification, or physically such as preparing an artificial liposome to reduce peptic destruction. The preferred route of administration is by injection. The compositions for oral use may contain one of more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay distintegration and absorption in the gastrointestinal tract and thereby provide a sustained action over a longer period. Similarly, suspensions, syrups, and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenxoate). Capsules may contain the active ingredient along or admixed with an inert solid diluent, e.g., calcium carbonate, calcium phosphate and kaolin. The injectable compositions are formulated as known in the art and may contain appropriate dispersing or wetting agents and suspending agents identical or similar to those mentioned above. The novel peptide of the present invention, AP-A, is preferably administered by injection.

A preferred pharmaceutcial composition of AP-A comprises the active ingredient in gelatin and phenol preservative. A further preferred pharmaceutical composition comprises for injection is sterile powdered lyophilized AP-A which in the dry form is stable at room temperature. The lyophilized powder may be packaged in vials containing hydrolyzed gelatin. AP-A must be reconstituted at the time of use by dissolving in a convenient volume of Sterile Water for injection or Sodium Chloride solution for injection in such a manner that the individual dose will be contained in 1-2 ml. of solution. The reconstituted solution should be refrigerated and used before decomposition or preferably within 24 hrs.

These pharmaceutical preparations may contain up to about 90% of the active ingredient in combination with the carrier or adjuvant.

The cardiotonic effective dosage of active ingredient employed for the treatment of congestive heart failure may vary depending on the severity of the condition being treated. However, in general, satisfactory results are obtained when anthopleurin-A is administered at an hourly dosgage of from about 0.01 µg. to about 5 µg/kg. of animal body weight, or in sustained release form for the period of time which is determined by those skilled in the art. Dosage forms suitable for internal use comprise from about 2 to about 360 µg. of the active compound in intimate admixture with a solid or liquid pharmaceutically acceptable carrier or diluent.

The preferred pharmaceutical compositions from the standpoint of preparation and ease of administration are injectable compositions, particularly those containing about 0.05 µg. of active ingredient per kg. of animal body weight.

Bioassay for Determining Positive Inotropic Effect

Bioassays of the solutions containing anthopleurin-A are performed on isolated atria of rat hearts. The atrium is separated from the rest of the heart and suspended in an isolated organ bath (20, 25, or 50 ml.) containing Krebs Ringer bicarbonate medium (pH 7.4) of the following composition in distilled deionized water (in mmoles): $Na^+$, 145; $K^+$, 6.02; $Ca^{+2}$, 1.22; $Mg^{+2}$, 1.33; $Cl^-$, 126; $HCO_3^-$, 25.3; $PO_4^{-3}$, 1.2; $SO_4^{-2}$, 1.33; and glucose, 5.5. The temperature of the organ bath is maintained at 30° C., and the Krebs-Ringer medium is continuously aerated with 95% $O_2$–5% $CO_2$.

The spontaneously beating atrial preparation is connected by a thin silk thread to a force-displacement transducer (Grass model FT.03), and the contractile movements are recorded on a six-channel polygraph Grass Model 7. The preparation is allowed to equilibrate under 750 mg. tension for 60 minutes prior to beginning to assay. After this equilibration, during which the preparations are washed out every 30 minutes, the spontaneous beat rate of the atria remains constant; the change during a 10-minute observation being less than 5 beats/min. The changes in contractile force and rate produced by the test solution containing anthopleurin-A is expressed as a percentage increase or decrease in tension and rhythm, with the period immediately preceding addition of test solution to the tissue bath as the baseline for comparison.

PHYSICAL AND CHEMICAL PROPERTIES OF AP-A

For the purpose of obtaining electrophoretic and amino acid analysis the anthopleurin-A obtained in Example 1 was rechromatographed on CM Sephadex C-25, Sephadex G-50 and G-10 according to the process set forth in Example 1, Steps c, d and e, respectively. The doubly purified material was subject to electrophoretic analysis using commercially available pre-cast 12% acrylamide gels and matched buffer systems obtained from Bio.Rad Laboratories, 32nd and Griffin, Richmond, California.

Isoelectric focusing gives the isoelectric point at a pH = 8.2. Disc gel electrophoresis with 12% polyacrylamide gel at pH 3.6 gave an $R_f$ value of 0.46 versus methyl green tracking dye. AP-A does not enter a basic gel at pH 8.9 indicating possible lack of available carboxyls. Sodium dodecyl sulfate (SDS) disc gel electrophoresis using a 10% gel indicated a m.w. of about 4,700 after incubation with dithioerythritol, using RNase A and pancreatic trypsin inhibitor (PTI) for comparison. The molecular weight is so low that these values are only approximate. AP-A was determined to be a peptide on the basis of positive ninhydrin spots obtained when a hydrolysate of AP-A was chromatographed.

Amino acid sequencing of the analytically pure S-carboxymethylated anthopleurin-A gave the following sequence (confirmed by amino acid analysis of a hydrolysate): Gly-Val-Ser-Cys-Leu-Cys-Asp-Ser-Asp-Gly-Pro-Ser-Val-Arg-Gly-Asn-Thr-Leu-Ser-Gly-Thr-Leu-Trp-Leu-Tyr-Pro-Ser-Gly-Cys-Pro-Ser-Gly-Trp-His-Asn-Cys-Lys-Ala-His-Gly-Pro-Thr-Ile-Gly-Trp-Cys-Cys-Lys-Gln.

This corresponds to a molecular weight of 5,183 daltons.

The abbreviated designations, which are used herein for the amino acid components are as follows:

| Abbreviated Designation | Amino Acid |
| --- | --- |
| Lys | lysine |
| His | histidine |
| Arg | arginine |
| Asp | aspartic acid |
| Thr | threonine |
| Ser | serine |
| Glu | glutamic acid |
| Gln | glutamine |
| Pro | proline |
| Gly | glycine |
| Ala | alanine |
| Cys | cysteine |
| Val | valine |
| Ile | isoleucine |
| Leu | leucine |
| Tyr | tyrosine |
| Trp | tryptophan |
| Asn | asparagine |

Anthopleurin-A is relatively stable at neutral and lower pH values and is very soluble in deionized water.

Anthopleurin-A can be further characterized by its pharmacological characteristics. The pharmacological characteristics indicate anthopleurin-A is about 200–1000x as potent as ouabain in positive inotropic effect, having an $ED_{50}$ at $1.1 \times 10^{-9}M$ on isolated guinea pig atrai. The $LD_{50}$ in mice (i.p.) is about 0.2–0.3 mg./kg. It does not show any chronotropic effect. At $3 \times 10^{-8}M$ concentrations of anthopleurin-A none of the following enzymes is inhibited: Na, K-ATPase; monoamine oxidase; catechol-O-methyltransferase; cyclic 3′,5′-nucleotide phosphodiesterase; nor does it affect the 3′,5′-cyclic AMP content of the guinea pig heart. Anthopleurin-A is not nearly as sensitive to $Ca^{++}$ concentration as is ouabain, and lowered external $K^+$ does not alter drug toxicity as with ouabain. Anthopleurin-A has been shown to be an effective cardiotonic agent in the isolated heart in rat, guinea pig, rabbit, cat and dog, and in the in situ heart in dog and cat. It has a negligible effect on blood pressure and no demonstrable mechanical effect on the isolated vascular muscle.

EXAMPLE 1

Isolation of Anthopleurin-A from Anthopleura xanthogrammica

Step a - Extraction

Anthopleura xanthogrammica (Brandt) specimens were collected, preserved in 95% ethanol and stored at 4° C. prior to extraction. Wet, drained anemones (5.5 kg.) were cut into <2 cm. pieces and homogenized batchwise in a blender for 5 minutes with 27 liters of 30% ethanol. This volume of ethanol includes the ethanol used to preserve the specimens. The mixture was allowed to stand for 1 week at 20° C. with occasional stirring, and then filtered through six layers of cheesecloth. The filtrate was flash evaporated at ≦40° C. to about 2.5 liters and partitioned with 12.5 liters of chloroform batchwise, by thorough agitation followed by centrifugation at 27,000 × g. for 30 minutes. This produced 13 g. of chloroform solubles, 19.5 g. of interface solids, and 256 g. (lyophilized weight) of water solubles containing anthopleurin-A.

Step b - Gel Permeation Chromatography

The 256 g. of crude water soluble extract, containing anthopleurin-A, was split into forty equal portions for chromatographic separation on Sephadex G-50 having an exclusion limit 30,000 (obtained from Pharmacia Fine Chemicals). A column 53 × 8.3 cm. containing 2,600 ml. of wet Sephadex G-50 (Vo = 825 ml.) was equilibrated with 0.1M $NH_4HCO_3$ saturated with chloroform (to prevent micro-organism growth). Fifty ml. of water containing 6.4 g. of crude water soluble extract containing anthopleurin-A was placed on the column and eluted with 0.1M $NH_4HCO_3$ at 8–9 ml./min. at room temperature. The following Table I sets forth in column 1 the range of Ve/Vo values of each fraction collected and in column 2 the weight of the residue resulting from the lyophilization of each fraction.

TABLE I

| Fraction | 1<br>Range of Ve/Vo values over which fraction was collected | 2<br>Weight of residue after lyophilization | 3<br>Concentration in ppm of test solution | 4<br>% increase in contractile force (time to max. in minutes) |
| --- | --- | --- | --- | --- |
| A | 0.95 to 1.18 | 0.215 g. | — | — |
| B | 1.18 to 1.84 | 0.107 g. | 4 | 0 |
|   |              |           | 40 | 100 (6 min.) |
| C | 1.84 to 2.57 | 0.163 g. | 0.4 | 120 (5 min.) |
| D | 2.57 to 3.08 | 5.034 g. | 4 | 0 |
|   |              |           | 40 | 30 (4 min.) |
| E | 3.08 to 3.38 | 0.73 g. | — | — |
| F | 3.38 to 4.10 | 0.04 g. | — | — |

The results of the bioassays for contractile force of the isolated rat atria, carried out as described in the section headed Bioassay, are set forth in Table I column 4. The results showed no activity in cuts A, E, and F. Fraction C contained ca. 99% of the cardiotonic activity. A total of 6.4 g. of fraction C was thusly produced from 256 g. of crude water solubles obtained in Step a.

Step c - Ion-exchange Chromatography

A 610 mg. portion of fraction C, obtained in Step b, was dissolved in 5 ml. of 0.03M $Na_x(PO_4)_y$ buffer at pH 7.5 and put on a 48 × 4 cm. column (Vo = 205 ml.) containing 600 ml. of wet cation exchange resin CM-Sephadex C-25 (obtained from Pharmacia Fine Chemicals) equilibrated with the same buffer saturated with chloroform. A stirred reservoir of 1,500 ml. of the buffer was connected to the column and after 110 ml. of buffer had flowed through the column, the reservoir volume was maintained constant by feeding with a 0.03M $Na_x(PO_4)_y$ buffer 0.5M in NaCl adjusted to pH 7.5 for gradient elution. Both solutions were saturated with chloroform. The flow rate of about 3 ml./min. was maintained and the run made at room temperature. The effluent was monitored using U.V. absorbance at 280 nm with a Model UA-5 Absorbance Monitor, obtained from Instrument Specialities Company, P.O. Box 5247, 4700 Superior Street, Lincoln, Nebraska 68505. The fraction having the Ve/Vo range between 2.99 and 3.39 and centered at Ve/Vo 3.17 was designated fraction G and found to be active according to the bioassay set forth under the heading Bioassay. Fraction G was lyophilized to give 610 mg. of material, containing anthopleurin-A admixed with salts. Fraction G was kept at $-20°$ C. and was used for all of the pharmacological studies.

Anthopleurin-A showed no signs of deterioration when kept at $-20°$ C. for a year as lyophilized fraction C, obtained in Step b, or as lyophilized fraction G. As fraction G, it was stable for at least 24 hours at 20.5° C. in $10^{-7}$M solutions at pH 4.55–7.80, but showed about 90% loss of cardiotonic activity at pH above 11.

Step d - Purification for Analysis

Fraction G, obtained in Step c, was further purified by gel filtration chromatography on Sephadex G-50 having an exclusion limit 30,000 (obtained from Pharmacia Fine Chemicals). A 50 ml. burette (54 × 1.2 cm) (Vo = 21.1 ml.) containing 52 ml. of wet G-50 was equilibrated with 0.017M $CH_3COOH$, 0.03M in NaCl saturated with chloroform. A solution of 102.6 mg. fraction G dissolved in 0.4 ml. $H_2O$ was put on the column and eluted at room temperature with the equilibrating solution. Fraction H was collected at Ve/Vo 1.66–2.16 centered at Ve/Vo 1.86. No U.V. absorbing material at 280 nm appeared before fraction H and only a trace appeared thereafter. Fraction H was lyophilized to give 20 mg. of anthopleurin-A (including the NaCl).

Step e - Desalting

The salt was removed by using a column packed with Sephadex G-10 having an exclusion limit of 700 obtained from Pharmacia Fine Chemicals). The 20 mg. of fraction H, obtained in Step d, was dissolved in 0.3 ml. of 10% NaCl and put on a 59 × 1.2 cm. column packed with 54 ml. wet Sephadex G-10 equilibrated with 0.017M acetic acid saturated with chloroform. The sample was followed by 0.5 ml. of 10% NaCl and then the equilibrating solution. Anthopleurin-A emerged completely and sharply at void volume (Ve/VO 0.93–1.12) and was salt free. It was immediately lyophilized to give 1.4 mg. of 30–80% pure anthopleurin-A.

Step f - Removal of Associated Inactive Polypeptides

The peptide (200 mg.) obtained by the process set forth in Steps a) to e), was dissolved in 10 ml. of distilled water and placed on a column (34 × 2.0 cm.) of Sephadex G-25, fine, in distilled water. Elution with distilled water produced the bulk of the active peptide (90%) 75% pure at Ve/Vo between 1.3 and 1.7, while the remainder of the active peptide was eluted pure with 0.2M $NH_4OAc$. The lyophilized peptide (113 mg.) was redissolved in distilled water and placed on a column 30 × 1.5 cm. of Cellex-SE cellulose (Bio.Rad Laboratories, Richmond, California), equilibrated with 0.05M pyridine adjusted to pH 2.7 with acetic acid. The active peptide was eluted pure by a linear gradient of 300 ml. each of 0.05M pyridine acetate pH 2.7 and 0.2M pyridine acetate pH 3.1 in an area corresponding to 0.1M pyridine acetate and lyophilized to give 80 mg. of >95% pure anthopleurin-A.

EXAMPLE 2

Sterile Suspension of AP-A for Injection

The anthopleurin-A obtained in Example 1 is mixed with sterile hydrozyled gelatin to the extent of 3.5 μg. anthopleurin-A to about 10 mg. hydrolyzed gelatin and packaged in sterile vials sealed in an atmosphere of nitrogen using conventional techniques. The AP-A is reconstituted at the time of use by the addition of 1 ml. sterile water. The injectable solution is suitable for administration once an hour for a body weight of 70 kg.

What is claimed is:

1. A peptide according to claim 1 having the amino acid sequence: Gly-Val-Ser-Cys-Leu-Cys-Asp-Ser-Asp-Gly-Pro-Ser-Val-Arg-Gly-Asn-Thr-Leu-Ser-Gly-Thr-Leu-Trp-Leu-Tyr-Pro-Ser-Gly-Cys-Pro-Ser-Gly-Trp-His-Asn-Cys-Lys-Ala-His-Gly-Pro-Thr-Ile-Gly-Trp-Cy-Cys-Lys-Gln.

2. A process for the preparation of anthopleurin-A from sea anemone, wherein the concentration of the intial alcohol extract is carried out at below 40° C and all other steps are carried at room temperature or below which comprises:
   a. extracting the sea anemones with water or with an aqueous-alcoholic mixture;
   b. subjecting the extract to gel filtration chromatography on a column of cross-linked dextran eluted with $NH_4HCO_3$ solution and collecting and lylophilizing the active fraction;
   c. subjecting the active fraction to chromatography on a column of cation exchange resin eluted with a phosphate buffer with a gradient of NaCl and collecting and lyophilizing the active fraction.

3. A process according to claim 2, which comprises:
   d. subjecting the active fraction obtained in c) to chromatography on a column of cross-linked dextran eluted with a NaCl solution and collecting and lyophilizing the active fraction;
   e. desalting the active fraction obtained in d) by chromatography on a column of cross-linked dextran eluted with dilute acetic acid and collecting and lyophilizing the active fraction.

4. The process according to claim 2, wherein the sea anemone is Anthopleura xanthogrammica.

5. The process according to claim 4 which comprises the following steps:
   a. extracting the sea anemone, *Anthopleura xanthogrammica*, with 30% aqueous ethanol;
   b. subjecting the extract to gel filtration chromatography on a column of cross-linked carboxymethyl dextran having an exclusion limit of 30,000 eluted with 0.1M $NH_4HCO_3$ solution and collecting and lyophilizing the active fraction;
   c. subjecting the active fraction to chromatography on a column of weakly acidic cation exchange resin eluted with 0.03M phosphate buffer at pH 7.5 and a gradient of 0.5N NaCl, collecting and lyophilizing the active fraction.

6. The process according to claim 5 which comprises:
   d. subjecting the active fraction obtained in c) to chromatography on a column of cross-linked dextran with an exclusion limit of 30,000 eluted with 0.017 M acetic acid which is 0.03M is NaCl and collecting and lyophilizing the active fraction;

e. desalting the active fraction obtained in d) by placing a solution of said active fraction on a column of cross-linked dextran with an exclusion limit of 700 followed by a solution of 20% sodium chloride solution and eluting with 0.017M acetic acid and collecting and lyophilizing the active fraction.

7. The pharmaceutcial preparation which comprises the peptide of claim 1 in admixture or conjunction with a pharmaceutically acceptable carrier.

8. The method of treating heart failure by administering a cardio effective amount of the peptide of claim 1.

* * * * *

UNITED STATES PATENT AND TRADEMARK OFFICE
CERTIFICATE OF CORRECTION

PATENT NO. : 4,059,694
DATED : November 22, 1977
INVENTOR(S) : TED R. NORTON, SHOJI SHIBATA, MIDORI KASHIWAGI It is certified that error appears in the above-identified patent and that said Letters Patent are hereby corrected as shown below:

Col. 2 line 31, "graphed" should read --graphy--.

Col. 4 line 64-65, "effects" should read --affects--.

Col. 5 line 17, "parenterially" should read --parenterally--

Col. 7 line 57, "atrai" should read --atria--.

Col. 9 line 51, "Ve/VO" should read --Ve/Vo--.

Col. 10 line 48, "Anthopleura xanthogrammica should be italicized.

Claim 1, line 1, "according to claim 1" should be deleted;

line 6, "Trp-Cy-Cys-Lys-Gln" should read --Trp-Cys-Cys-Lys-Gln--;

Claim 2, line 10, "lylo" should read --lyo--.

Signed and Sealed this

Eleventh Day of April 1978

[SEAL]

Attest:

RUTH C. MASON
Attesting Officer

LUTRELLE F. PARKER
Acting Commissioner of Patents and Trademarks